United States Patent [19]

Nagashima et al.

[11] Patent Number: 4,616,636

[45] Date of Patent: Oct. 14, 1986

[54] LIGHT EMISSION SWITCHING CIRCUIT FOR LARYNX STROBOSCOPE

[75] Inventors: Hironobu Nagashima; Hiroshi Koyama, both of Tokyo, Japan

[73] Assignee: Asahi Kogaku Kogyo Kabushiki Kaisha, Tokyo, Japan

[21] Appl. No.: 756,121

[22] Filed: Jul. 18, 1985

[30] Foreign Application Priority Data

Jul. 27, 1984 [JP] Japan .................. 59-156572

[51] Int. Cl.⁴ .......................... A61B 1/00; G01P 3/40
[52] U.S. Cl. .................. 128/23; 315/241 S; 356/23
[58] Field of Search ............. 128/23; 315/241 S; 356/23

[56] References Cited

U.S. PATENT DOCUMENTS 3,026,449  3/1962  Rappaport ................ 128/23 X

Primary Examiner—William H. Grieb
Attorney, Agent, or Firm—Sughrue, Mion, Zinn, Macpeak & Seas

[57] ABSTRACT

A light emission switching circuit for use in a larynx stroboscope in which switching between a mode in which a stroboscopic lamp is flashed in synchronism with vibration of vocal cords and a mode in which the lamp is flashed at a fixed frequency is effected quickly in such a manner that there is no gap in light output at the time of switching. A detection output signal is produced when the frequency of a vocal cords vibration signal falls below a predetermined frequency, typically, about 50 Hz. When this signal is present, a switch circuit is controlled so as to connect the output of a fixed-frequency oscillator to drive the stroboscope. When the signal is absent, a pulse signal synchronous with the vocal cords vibration signal is employed to drive the stroboscopic lamp.

4 Claims, 5 Drawing Figures

LIGHT EMISSION SWITCHING CIRCUIT FOR LARYNX STROBOSCOPE

BACKGROUND OF THE INVENTION

The present invention relates to a light emission switching circuit for use in a larynx stroboscope.

A larynx stroboscope is a device in which a flash lamp is made to emit light in synchronization with the vibration of a patient's vocal cords and is used to examine and diagnose vocal cord polyps, cancer of the larynx, etc. In conducting examination with the device, it is of course necessary to direct the output light of the flash lamp onto the vocal cords under examination. This is carried out with the vocal cords still. That is, the operator of the device operates a switch or the like to cause the flash lamp to emit light at a predetermined fixed frequency so as to illuminate the part under examination. Then, during examination, the light emission mode is switched according to whether or not the vocal cords are vibrating. That is, when the vocal cords are vibrating during examination, the flash lamp is caused to emit light in synchronization with their vibration, while when the vocal cords are still, the flash lamp emits light with a predetermined fixed period.

Heretofore, in order for the device to determine when the vocal cords are still, it has been the practice to detect when the average level of a vocal cords vibration signal (a signal following the vibration of the vocal cords) becomes lower than a reference level. However, because the detection time is relatively long, sometimes the vocal cords are completely still before detection is accomplished. In other words, the vocal cords may have stopped vibrating a significant time before the mode in which light is emitted synchronously with the vocal cords vibration is switched over to the mode in which light is emitted with the predetermined period. Also, with the conventional circuit, the light emission of the flash lamp is stopped momentarily immediately before the switching operation. Recently, it has been found desirable to record the motion of the vocal cords on video tape, and in this case the momentary suspension of light emission greatly lowers the quality of the resultant image.

SUMMARY OF THE INVENTION

In general, the vocal cords vibrate predominantly in a range of frequencies higher than 50 Hz. Immediately before the vibration stops, however, the vibration frequency sharply decreases. Therefore, the suspension of the vibration of the vocal cords can be predicted by detecting the fact that the vibration frequency has considerably decreased.

Based on this fact, in accordance with the invention, the suspension of vocal cords vibration is predicted and the light emission mode switched accordingly. More specifically, when the interval of a pulse signal synchronous with a vocal cords vibration signal exceeds a predetermined value, it is taken that the vocal cords vibration will be suspended soon. Therefore, when the interval of the pulse signal exceeds the predetermined value, the light emission mode of the flash lamp is switched over to the light emission mode effected at the predetermined frequency, thereby preventing momentary suspension of the light emission of the flash lamp which would otherwise be caused immediately before the switching operation.

Thus, the invention improves the conventional system of detecting the presence or absence of the vocal cords vibration signal, and by preventing momentary suspension of light emission, allows the motion of the vocal cords to be recorded on video tape with an excellent image quality.

DESCRIPTION OF THE PREFERRED EMBODIMENTS

Figure 1:
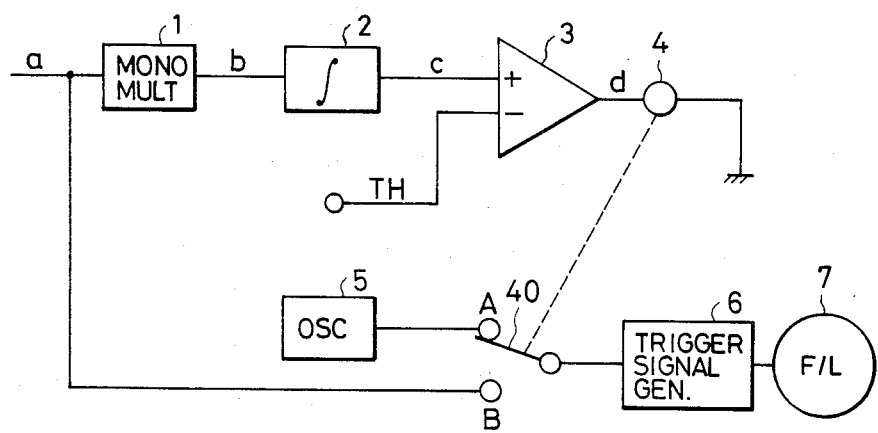
FIG. 1 is a block diagram showing a preferred embodiment of the invention.
Figure 2A:
FIGS. 2a-2d show a timing chart showing output signals in the circuit shown in FIG. 1.
Figure 2B:
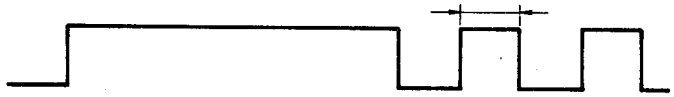
Figure 2C:
Figure 2D:
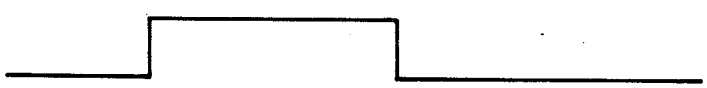

FIG. 1 is a block diagram showing a preferred embodiment of a circuit of the invention.

A pulse signal a synchronous with a vocal cords vibration signal is applied to a monostable multivibrator 1, the output signal b of which is applied to an integrating circuit 2. The output signal c of the integrating circuit and a constant level signal having a level TH are applied to respective inputs of a comparator 3 where they are subjected to comparison. When the output signal c of the integrating circuit 2 is smaller than TH, the output signal d of the comparator 3 is at the low level. In this case, the armature 40 of a relay 4 is engaged with its contact A, and therefore the output (a pulse signal having a predetermined frequency) of an oscillating circuit 5 is applied to a trigger signal generating circuit 6. When the output signal c of the integrating circuit 2 is equal to or larger than TH, the output signal d of the comparator 3 is at the high level and then the armature 40 of the relay 4 is tripped over to its contact D, in which case the pulse signal a synchronous with the vocal cords vibration signal is applied to the trigger signal generating circuit. In response to the input signal, the trigger signal generating circuit 6 produces a trigger signal which is applied to a flash lamp 7. The flash lamp 7 emits light in synchronization with the trigger signal thus applied.

FIG. 2 is a timing chart showing the abovedescribed output signals. In FIG. 2, reference character a designates the pulse signal synchronous with the vocal cords vibration signal; b, the output signal of the monostable multivibrator 1, which is held at the high level when the pulse interval of the vocal cords vibration signal is T (seconds) or shorter, and which, when the pulse interval is longer than T, is held at the high level for a period T from the rise of the pulse and set to the low level thereafter; c, the output signal of the integrating circuit 2 obtained by integrating the signal b, which cannot reach the predetermined level TH in the period of T; and d, the output signal of the comparator 3, which is raised to the high level only when the signal c is at the predetermined level TH or higher.

As is apparent from FIG. 2, when the pulse interval of the pulse signal a synchronous with the vocal cords vibration signal is T or shorter, the output signal d of the comparator 3 is at the high level, and when it is longer than T, the output signal d is at the low level. Accordingly, as is clear from the arrangement of the circuit in FIG. 1, when the output signal d of the comparator 3 is at the high level, the flash lamp 7 emits light in synchronization with the vocal cords vibration signal, and when the signal d is at the low level, the flash lamp 7 emits light at a predetermined frequency. That is, the pulse interval of the signal synchronous with the vocal cords vibration signal increases immediately before the vocal cords vibration signal disappears, and therefore the mode where the light emission of the flash lamp 7 is synchronous with the vocal cords vibration signal and the mode where the light emission of the flash lamp 7 is at the predetermined frequency can be selected according to whether or not the vocal cords vibration signal is present, that is, according to the detection of the pulse interval.

According to the invention, when the suspension of the vibration of the vocal cords has been predicted, the mode where light emission is synchronous with the vocal cords vibration and the mode where light emission occurs at the predetermined frequency are switched. That is, the light emission switching circuit of the invention quickly produces a signal required for the switching operation. Therefore, the momentary suspension of light emission, which would otherwise occur immediately before the switching operation, is effectively prevented.

We claim:

1. A light emission switching circuit for use in a larynx stroboscope, comprising:
    means for detecting the presence of vocal cords vibration according to a pulse period of a first pulse signal synchronous with said vocal cords vibration;
    oscillator means for generating a second pulse signal having a constant frequency; and
    switching means for selecting, in accordance with an output of said detecting means, as an output for driving a flash lamp of said stroboscope, one of said first and second pulse signals, wherein when vocal cords vibration is detected by said detector means, light is emitted in synchronism with said vocal cords vibration, and when no vocal cords vibration is detected, light is emitted at said constant frequency.

2. The light emission switching circuit as claimed in claim 1, wherein said detecting means comprises means for indicating suspension of said vocal cords vibration when a pulse period of said first pulse signal is below a constant value.

3. The light emission switching circuit as claimed in claim 1, wherein said detecting means comprises:
    a monostable multivibrator receiving said first pulse signal as a trigger input thereto;
    an integrating circuit receiving as an input an output signal of said monostable multivibrator; and
    a comparator for comparing an output signal of said integrating circuit with a constant level signal, thereby to generate an output signal for indicating whether or not said vocal cords are vibrating, an output of said comparator being applied to a control input of said switching means.

4. The light emission switching circuit as claimed in claim 3, wherein the level of said constant level signal is set at a level of said output signal of said integrating circuit for which a frequency of said first pulse signal is at a frequency indicative that cessation of vocal cords vibration is imminent.

* * * * *